(12) United States Patent
Obrigkeit

(10) Patent No.: US 8,585,679 B2
(45) Date of Patent: Nov. 19, 2013

(54) EVEN-FLOW MULTI-STAGE CANNULA

(75) Inventor: Kevin G. Obrigkeit, Plymouth, MI (US)

(73) Assignee: Terumo Cardiovascular Systems Corp., Ann Arbor, MI (US)

( * ) Notice: Subject to any disclaimer, the term of this patent is extended or adjusted under 35 U.S.C. 154(b) by 1078 days.

(21) Appl. No.: 12/108,579

(22) Filed: Apr. 24, 2008

(65) Prior Publication Data

US 2009/0270816 A1    Oct. 29, 2009

(51) Int. Cl.
*A61M 25/00* (2006.01)

(52) U.S. Cl.
USPC ............................ 604/523; 604/6.16; 604/264

(58) Field of Classification Search
USPC ........ 604/43, 264, 523, 6.16, 27, 30, 35, 507, 604/508, 266, 532, 537
See application file for complete search history.

(56) References Cited

U.S. PATENT DOCUMENTS

| | | | |
|---|---|---|---|
| 4,129,129 A * | 12/1978 | Amrine | 600/16 |
| 4,639,252 A | 1/1987 | Kelly et al. | |
| 4,787,882 A | 11/1988 | Claren | |
| 5,769,828 A | 6/1998 | Jonkman | |
| 6,152,911 A | 11/2000 | Giannoble | |
| 6,936,041 B2 | 8/2005 | Viitala | |
| 7,566,316 B2 * | 7/2009 | McGuckin et al. | 604/6.16 |
| 2006/0004316 A1 * | 1/2006 | Difiore et al. | 604/6.16 |

OTHER PUBLICATIONS

MEDTRONIC, MC2X, Three Stage Venous Cannulae, Performance Under Pressure, 2005.*

* cited by examiner

*Primary Examiner* — Kevin C Sirmons
*Assistant Examiner* — Laura Schell
(74) *Attorney, Agent, or Firm* — Gael Diane Tisack; Darryl Newell; MacMillan, Sobanski & Todd

(57) ABSTRACT

A single-lumen, multi-stage cannula particularly adapted for venous drainage during cardiac surgery includes a first stage comprising a longitudinal tubular tip having a first plurality of fenestrations to provide an axial flow at a proximal end of the tip. A second stage coaxial with the first stage comprises a nozzle section having an outer lumen wall and an inner annular wall. A central passage disposed within the inner annular wall continues the axial flow from the first stage. A plurality of outer passages is disposed between the outer lumen wall and the inner annular wall so that the inner annular wall isolates the central passage from the outer passages. The outer lumen wall includes a plurality of second fenestrations, wherein each second fenestration supplies fluid from a second region outside the cannula to a respective outer passage. The outer passages have respective outlets arranged to provide an injected flow substantially parallel to the axial flow. At least an initial portion of the central lumen of a proximal tube has an inside diameter greater than a diameter of the central passage. The central lumen continues the axial flow and receives the injected flow annularly injected around and substantially parallel with the axial flow.

16 Claims, 4 Drawing Sheets

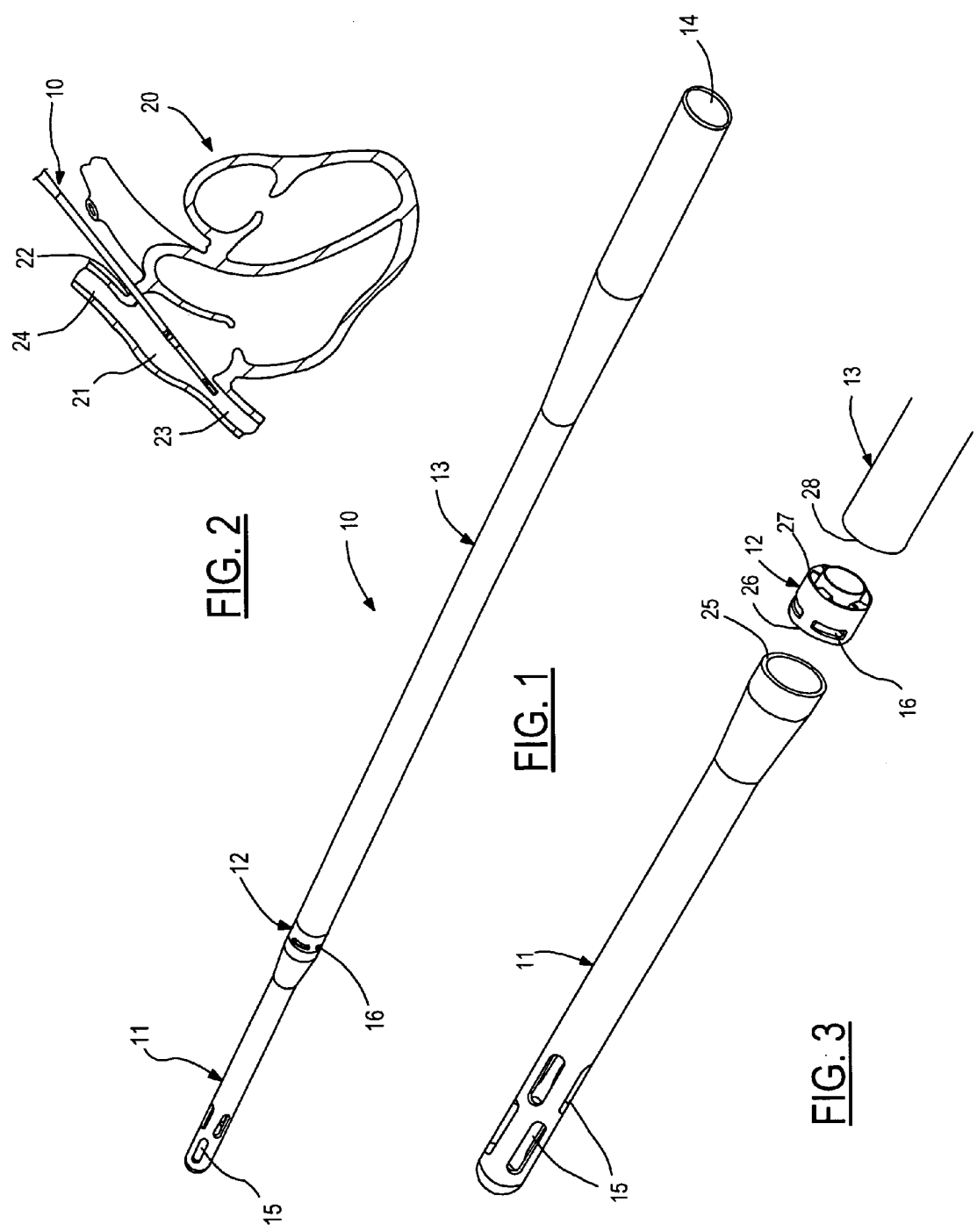

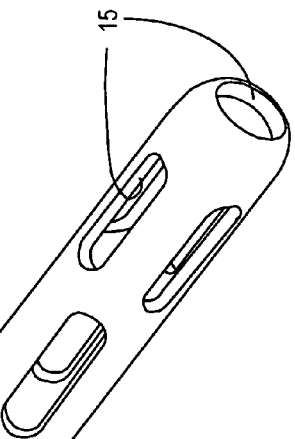
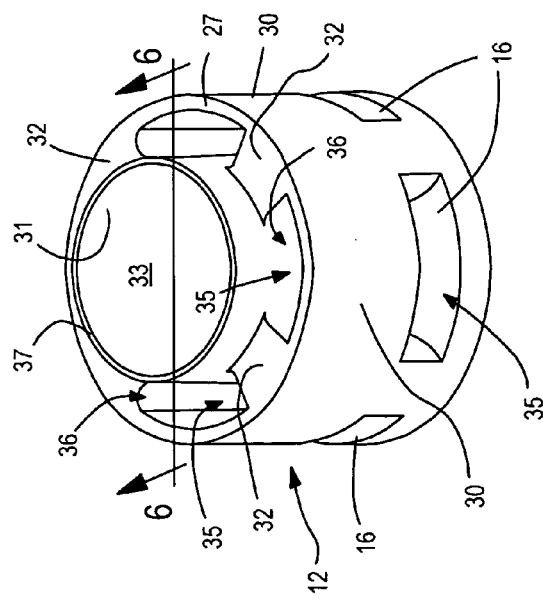
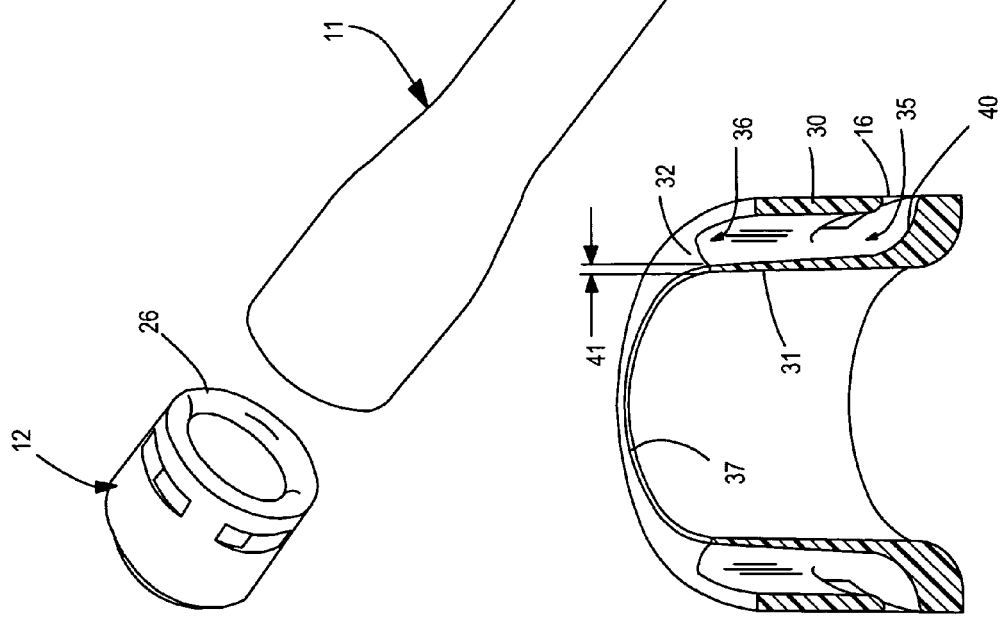

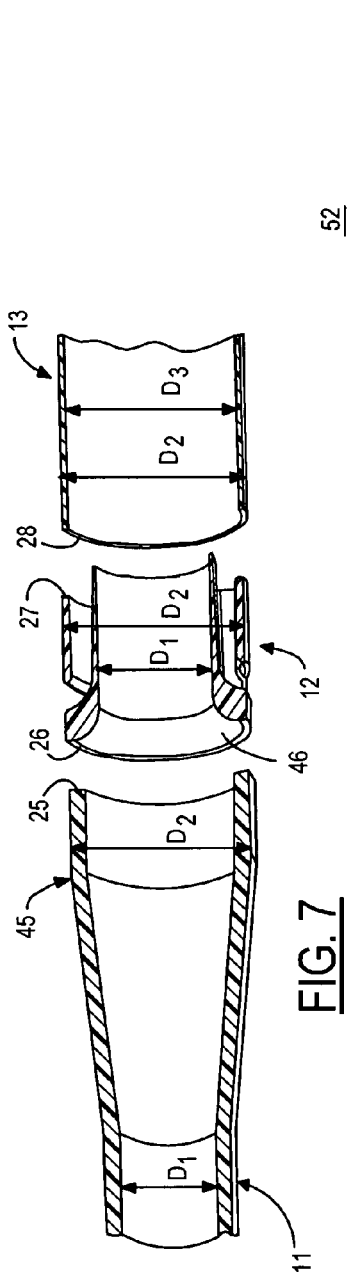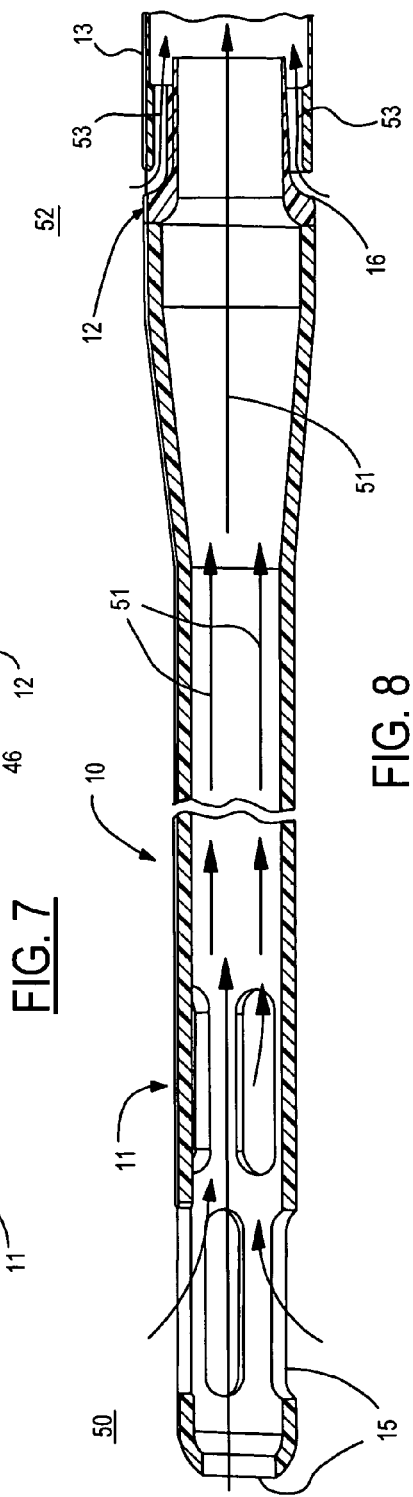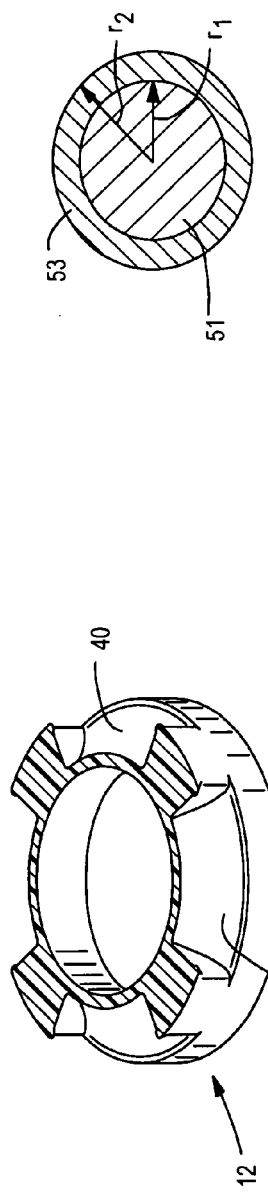
FIG. 7
FIG. 8
FIG. 9
FIG. 10

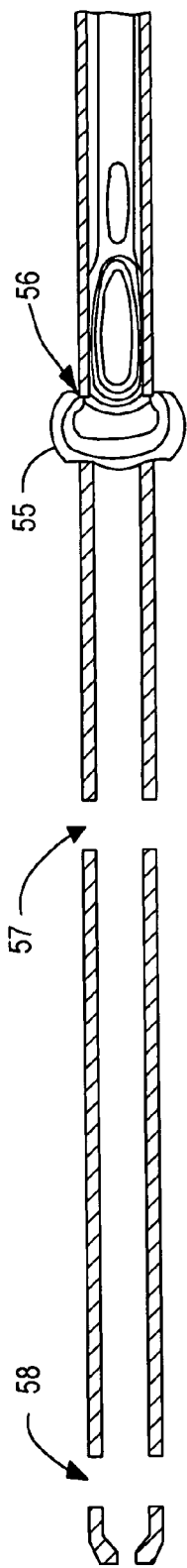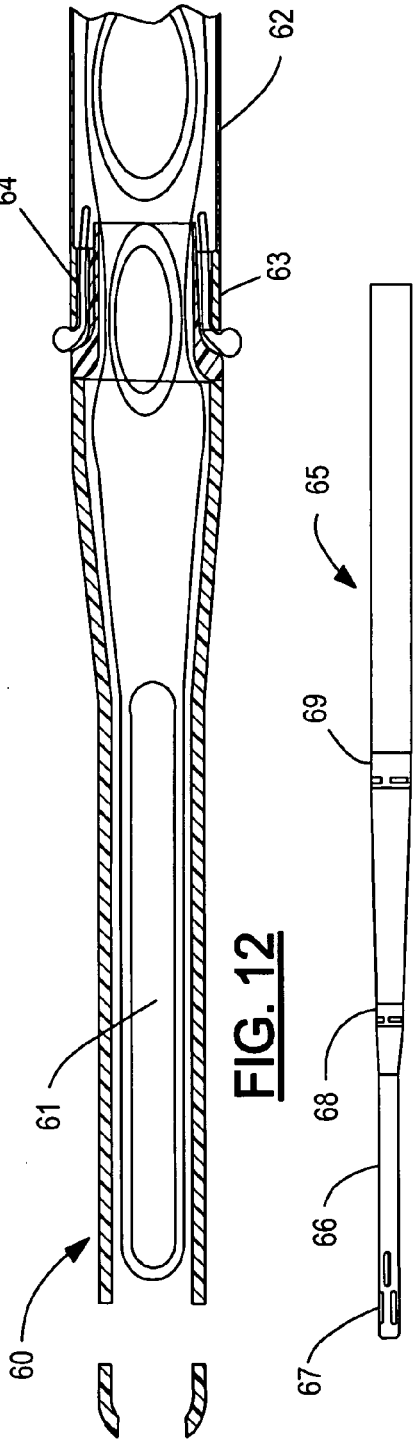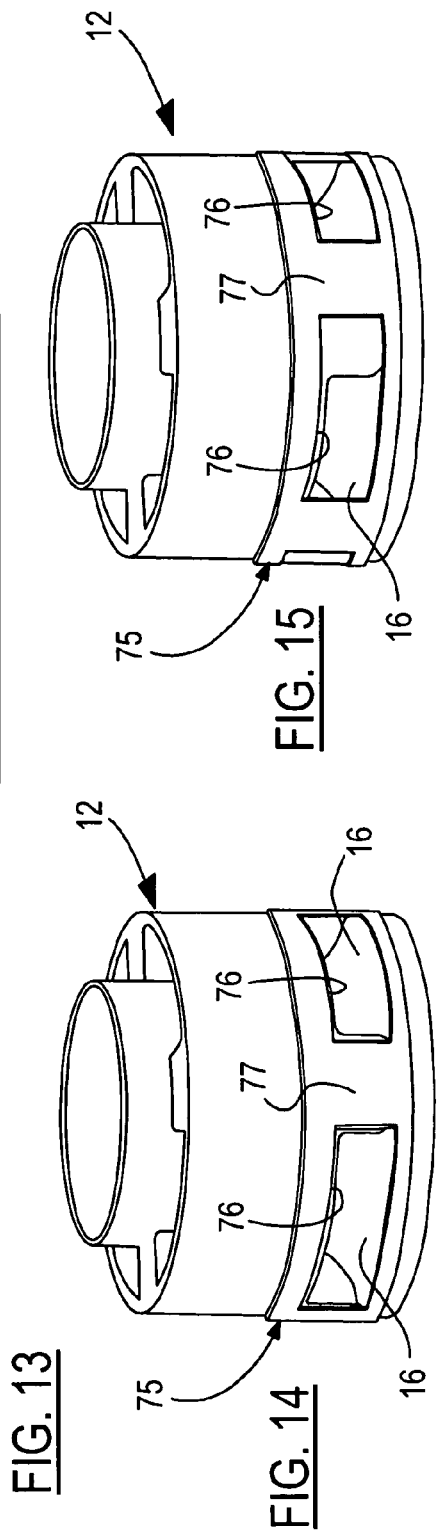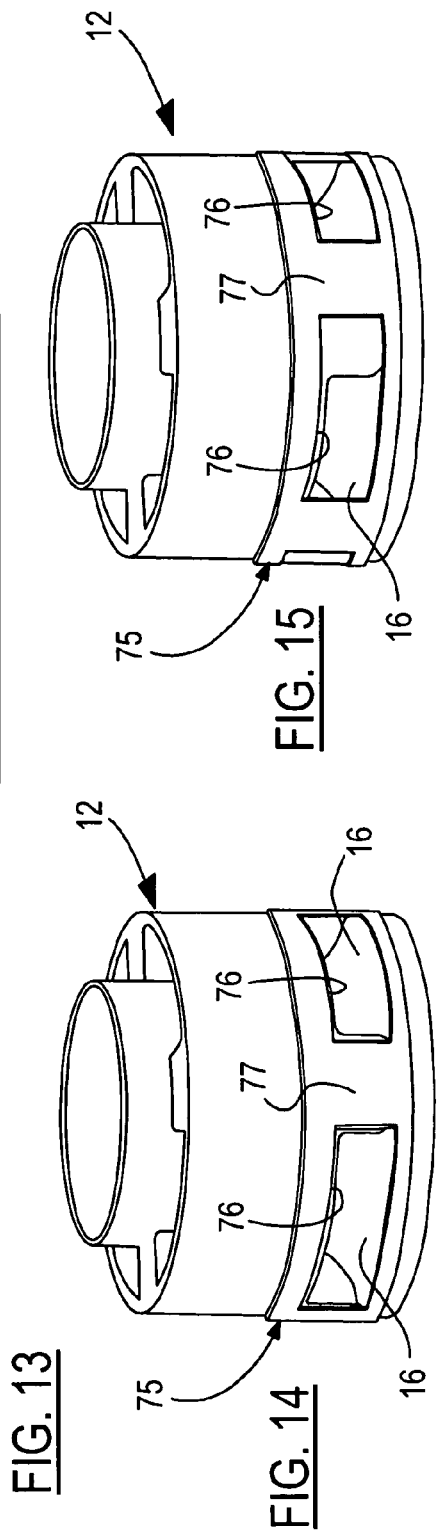

US 8,585,679 B2

EVEN-FLOW MULTI-STAGE CANNULA

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to a venous return cannula, and, more specifically, to a multi-stage cannula generating an even flow from multiple inlets along the length of the cannula.

A venous drainage cannula (also called a catheter) is used during cardiac surgery to remove (i.e., drain) blood from a patient using suction provided by gravity siphon or a pump coupled to the cannula. The removed blood is conducted to perfusion equipment which treats the blood by removing carbon dioxide, infusing oxygen, and heating or cooling the blood before returning it to the patient. It has become common to use a multi-stage cannula having separate sets of openings along the longitudinal body of the cannula to collect blood from locations near both the inferior vena cava and the superior vena cava, as is shown in U.S. Pat. No. 4,129,129 to Amrine, for example.

One reason why drainage from two locations is desirable for collecting blood during coronary artery bypass surgery is that blood flows into the right atrium in two directions (i.e., from the superior and inferior vena cava). The areas containing fenestrations (i.e., holes) are often referred to as baskets. Use of two or more separated baskets allow for a more dispersed intake of blood, helping to avoid pockets of blood that become stagnant and do not circulate through the perfusion circuit. The drainage flow volume passing through each basket depends upon the pressure drop at each stage of the cannula. Approximately equal amounts of blood are desired to be collected at each basket, so that the aggregate cross-sectional area of the fenestrations of each basket has been kept close to equal. Nevertheless, the volume of blood collected by the cannula from each respective basket has not been equal due to differences in pressure drop. Specifically, the volume collected at the first stage of a prior art cannula has been significantly less than at the second stage. The basket closest to the source of suction (e.g., the second stage in a two stage cannula) experiences a greater pressure drop and therefore provides the majority of the intake volume. Once it is inside the lumen of the cannula, blood passing through the fenestrations of the first stage is exposed to a bolus of blood that has already released pressure after passing through the second stage basket. The smaller pressure drop across the first stage results in a lowered intake so that the total volume of blood supplied by the cannula is unequally distributed between the stages.

Normal blood flow for a patient is typically characterized by substantially equal blood volumes flowing from the inferior and superior vena cava (e.g., in many adult studies, the inferior vena cava has been found to convey up to 65% of total cardiac output. Individual variations in age, size, and shape, or variations in specific surgical procedure that may be performed may result in slightly different flow ratios. An even flow as described herein includes, without limitation, flow ratios from 1-to-1 up to 2-to-1 or more.

The "flow coefficient" of a device is a measure of its ability to pass a fluid therethrough. It relates the fluid flow in volume per unit time to the inlet and outlet pressures and the pressure drop. Since prior art cannulae with multiple stages have had unequal pressure drops at the respective stages, manipulating the flow coefficients would not be successful in obtaining the desired flow ratios. When desiring to obtain even flow volumes from the regions of both baskets, it has been necessary to use two separate single-stage cannulae so that collection at one location does not affect the pressure drop at the other location. However, the use of dual cannulae requires a larger incision or multiple incisions. Therefore, it would be desirable to optimize the percentage of flow between multiple stages of a cannula, especially to allow control of a flow ratio to match blood collection to the characteristics of a particular patient and procedure so that blood is efficiently collected without creating stagnant pockets or collapsing anatomical structures onto any fenestrations.

SUMMARY OF THE INVENTION

This invention overcomes the limitations of prior art multi-stage cannulae by protecting a particular stage from the pressure drop associated with a subsequent stage. A nozzle isolates the flows and injects them in a common direction toward a common outlet. Various flow ratios can be achieved in part by adjusting the relative nozzle flow characteristics.

In one aspect of the invention, a single-lumen, multi-stage cannula particularly adapted for venous drainage during cardiac surgery is provided. A first stage comprises a longitudinal tubular tip having a first plurality of fenestrations disposed at a distal end of the tip for supplying fluid from a first region outside the cannula to provide an axial flow at a proximal end of the tip. A second stage coaxial with the first stage comprises a nozzle section having an outer lumen wall and an inner annular wall. A central passage is disposed within the inner annular wall. The central passage continues the axial flow from the first stage. A plurality of outer passages is disposed between the outer lumen wall and the inner annular wall so that the inner annular wall isolates the central passage from the outer passages. The outer lumen wall includes a plurality of second fenestrations, wherein each second fenestration supplies fluid from a second region outside the cannula to a respective outer passage. The outer passages have respective outlets arranged to provide an injected flow substantially parallel to the axial flow. A proximal tube coaxial with the second stage has a central lumen delivering a drainage output of the cannula. The central lumen continues the axial flow and receives the injected flow annularly injected around and substantially parallel with the axial flow.

BRIEF DESCRIPTION OF THE DRAWINGS

FIG. 1 is a perspective view of a cannula according to one embodiment of the present invention.

FIG. 2 is a section view of a heart having a cannula inserted for draining venous blood.

FIG. 3 is a partial, exploded view of the cannula of FIG. 1.

FIG. 4 is a perspective, exploded view of the first and second stages of FIG. 1.

FIG. 5 is a perspective view showing the second stage nozzle in greater detail.

FIG. 6 shows a central cross section of the nozzle of FIG. 5.

FIG. 7 is a partial, exploded view of the cannula of FIG. 1 seen in cross section.

FIG. 8 is a cross-sectional plan view showing the flows of the first and second stages.

FIG. 9 shows a horizontal cross section of the nozzle.

FIG. 10 shows a cross section of the nozzle outlet to illustrate the relative proportions of the combined stages.

FIG. 11 is a flow velocity map for a prior art multi-stage cannula.

FIG. 12 is a flow velocity map illustrating the even flow obtained by the present invention.

FIG. 13 is a plan view showing a three stage cannula of the present invention.

FIG. 14 is a perspective view of an alternative embodiment of the nozzle for providing a variable flow coefficient.

FIG. 15 is a perspective view of the embodiment of FIG. 14 with the sleeve rotated for providing a reduced flow coefficient.

DETAILED DESCRIPTION OF PREFERRED EMBODIMENTS

Referring to FIG. 1, a cannula 10 includes a first stage 11, second stage 12, and a proximal tube 13. A continuous single lumen 14 is provided from end-to-end within cannula 10 and receiving blood through a first plurality of fenestrations 15 in first stage 11, and a second plurality of fenestrations 16 in second stage 12.

FIG. 2 shows a heart 20 having a right atrium 21 receiving cannula 10 through an incision 22. The first stage of cannula 10 is typical positioned to receive blood from an inferior vena cava 23 while the second stage drains blood from right atrium 21 and superior vena cava 24. In prior art cannulae, pressure drop at the second stage basket has limited the flow from the first stage to an extent that makes it difficult to match blood drainage by the cannula to the normal anatomical flow volumes supplied by the inferior and superior vena cava. Typically, the ratio of flow from the inferior vena cava to the superior vena cava is approximately even (i.e., a 1 to 1 ratio) or is slightly biased with more coming from the inferior vena cava (i.e., a ratio of 3-to-2). Reducing the area of prior art fenestrations at the second stage basket in order to limit the second stage flow undesirably creates an increased velocity at the second stage basket and a greater tendency for the surrounding structure to collapse onto the cannula. The second stage nozzle of the present invention overcomes these difficulties.

As shown in FIGS. 3 and 4, cannula 10 may be comprised of separately molded pieces for first stage 11, second stage 12, and proximal tube 13. Each component may be formed of a biocompatible thermoplastic such as polyvinylchloride, nylon, or the like. An end surface 25 is provided on first stage 11 for joining to a surface 26 at one end of second stage 12. A circumferential surface 27 is provided at the other end of second stage 12 for joining with an end surface 28 of tube 13. The parts may be adhesively bonded, ultrasonically welded, or otherwise joined using any known method for producing a leak-proof joint.

FIG. 5 shows second stage 12 in greater detail. An outer lumen 30 is joined to an inner annular wall 31 by a plurality of beam sections 32. A central passage 33 is formed within inner annular wall 31. Fenestrations 16 are each connected to a respective outer passage 35 that are each disposed between outer lumen wall 30 and inner annular wall 31. Thus, inner annular wall 31 isolates central passage 33 from outer passages 35. Each fenestration 16 supplies fluid from a region outside the cannula into a respective outer passage 35. Passages 35 have respective outlets 36 arranged to provide an injected flow of the fluid which is substantially parallel to an axial flow through central passage 33. In one preferred embodiment, inner annular wall 31 has a downstream, termination end 37 that extends beyond outlets 36 of passages 35 to increase isolation between the injected flow and the axial flow(s) from previous stages.

Since fenestrations 16 are oriented perpendicularly with respect to the main axial flow through the cannula and since the outlets 36 of the outer passages 35 are oriented substantially parallel to the axial flow, each outer passage 35 includes a curved wall portion 40 for guiding the fluid received through the fenestrations into the injected parallel flow as shown in FIG. 6. In addition, inner annular wall 31 preferably has a narrowing wall thickness 41 to smoothly blend the injected flow with the axial flow output from the nozzle. The narrowing thickness portion may extend the entire length of passage 35 or at least between outlets 36 and termination 37 of wall 31.

In a preferred embodiment, fenestrations 16 are substantially equally spaced circumferentially around outer lumen wall 30 and each outer passage 35 is axially (i.e., longitudinally) aligned with its respective fenestration 16. Each outer passage 35 preferably has a cross-sectional area perpendicular to its flow direction (i.e., a flow profile) that is substantially constant from its fenestration 16 to its outlet 36.

FIG. 7 shows an exploded cross-sectional view showing bonding surfaces 25-28 in greater detail. Over most of its axial length, first stage 11 has an inner diameter $D_1$. Likewise, central passage 33 of second stage nozzle 12 has an inner diameter equal to $D_1$ so that the first stage axially flow can flow smoothly through the respective stages. Second stage nozzle 12 has an outer diameter $D_2$ encompassing both the axial and injected flows. Consequently, $D_2$ is greater than $D_1$. In order to provide an appropriate outer surface for the cannula, first stage 11 has a downstream end section 45 growing to an outer diameter $D_2$ for proper bonding with second stage nozzle 12. Central passage 33 may include a funnel-shaped section 46 to maintain smooth flow at the transition between the first and second stages. Proximal tube 13 likewise has an outer diameter $D_2$ to match second stage nozzle 12 to facilitate bonding. Tube 13 has an inner diameter $D_3$ appropriate sized to receive both the axial and injected flows without substantially modifying them.

FIG. 8 shows the fluid flows of the present invention. With cannula 10 inserted into a heart, fenestrations 15 in first stage 11 receive a blood flow from a region 50 such as the inferior vena cava. As a result of suction applied to cannula 10 from a vacuum pump or gravity siphon drainage in a perfusion circuit, a pressure drop is seen at fenestrations 15 so that an inflow of blood provides an axial flow 51 within the interior lumen of first stage 11. Axial flow 51 continues within the central passage of the second stage nozzle having a substantially constant flow cross-sectional diameter. Second stage nozzle 12 also receives blood from a second region 52 such as the superior vena cava as a result of a pressure drop seen at fenestrations 16 likewise created by the vacuum pump or gravity siphon. An injected flow 53 enters fenestrations 16 and is redirected and then injected into proximal tube 13 annularly surrounding axial flow 51. Gradually curved walls 40 for reorienting flow 53 are shown in greater detail in FIG. 9.

Since the pressure drops corresponding to each stage have been substantially equalized, relative blood volumes from the stages is more a function of the flow coefficients for each flow path. When it is desired to have a substantially even flow between the stages, substantially equal flow coefficients are provided for each flow path. The flow coefficients depend upon various factors such as size and orientation of fenestrations and the minimum cross-sectional areas of each respective flow path.

As a simplistic, first-order approximation, the overall flow coefficients for each flow in a second stage nozzle are approximated by the respective flow profiles (i.e., minimum cross-sectional areas) for each path at the output of the nozzle. As shown in FIG. 10, axial flow path 51 has a circular cross section with a radius $r_1$. Injected flow 53 has a ring-shaped cross section between radii $r_1$ and $r_2$. Substantially equal flow coefficients are obtained when the respective cross-sectional areas are approximately equal. The areas are equal when $r_2$ is 1.4 times as great as $r_1$. A slightly greater outer radius $r_2$ may be used to compensate for the cross-sectional area occupied by beams 32. Furthermore, if a ratio other than an even ratio is desired (e.g., due to the characterization of anatomical blood flow), the relative radii of the inner annular wall and outer lumen can be similarly adjusted. For example, to obtain a 3-to-2 ratio such that the axial flow from the first stage comprises 60% of the total flow and the injected flow comprises 40% of the total flow, then $r_2$ would be about 1.29 times as great as $r_1$. Alternatively, if the inner flow is desired to comprise 65% of the total flow, then $r_2$ equals about 1.24 times $r_1$. The exact sizes and ratios of the flow paths would typically be determined using fluid dynamics models.

FIG. 11 illustrates fluid flow velocities obtained in a multi-stage cannula of the prior art having conventional fenestrations for each stage. Contour lines 55 represent points having equal flow velocities. At a third stage 56, the closely spaced contour lines 55 indicate increasing flow velocity as fluid enters stage 56. Stages 57 and 58 upstream from stage 56 do not experience the same pressure drop and have relatively low flow velocities since a low volume of fluid is collected at those stages.

FIG. 12 shows flow velocities obtained according to the present invention. A first stage 60 generates an axial flow 61 having a flow velocity which maintains a substantially constant velocity as it passes into a proximal tube 62 past a nozzle 63 for the second stage. A flow 64 injected by nozzle 63 smoothly blends with flow 61 in tube 62.

FIG. 13 shows an alternative embodiment of the invention having a three stage cannula 65 with a first stage 66 employing conventional fenestrations 67. A second stage 68 comprises a nozzle of the present invention and introduces an increased diameter of cannula 65. A third stage 69 comprises a slightly larger nozzle of the present invention and introduces a further increase in the inner and outer diameters of cannula 65 to accommodate the cross section of all the combined flows.

FIG. 14 shows a modification of the invention for providing a manually adjustable aggregate flow coefficient for the outer passages of the nozzle to adjust the ratio of the axial flow to the injected flow. Thus, a rotatable sleeve 75 is provided on the outer surface of nozzle 12 having apertures 76 in alignment with fenestrations 16. By circumferentially rotating sleeve 75 as shown in FIG. 15, a bridge portion 77 selectively covers a portion of each fenestration 16 thereby reducing their aggregate cross-sectional area. The reduction in the corresponding flow coefficients reduces the corresponding injected flow by a corresponding amount.

What is claimed is:

1. A single-lumen, multi-stage cannula comprising:
a first stage comprising a longitudinal tubular tip having a first plurality of fenestrations disposed at a distal end of the tip for supplying fluid from a first region outside the cannula to provide an axial flow at a proximal end of the tip;
a second stage coaxial with the first stage comprising a nozzle section having an outer lumen wall and an inner annular wall, wherein a central passage is disposed within the inner annular wall, wherein the central passage continues the axial flow from the first stage, wherein a plurality of outer passages are disposed between the outer lumen wall and the inner annular wall so that the inner annular wall isolates the central passage from the outer passages, wherein the outer lumen wall includes a plurality of second fenestrations, wherein each second fenestration supplies fluid from a second region outside the cannula to a respective outer passage, and wherein the outer passages have respective outlets arranged to provide an injected flow substantially parallel to the axial flow; and
a proximal tube coaxial with the second stage and having a central lumen, wherein an initial portion of the central lumen continues the axial flow and receives the injected flow annularly injected around and substantially parallel with the axial flow, and wherein a proximal end of the central lumen delivers a drainage output of the cannula comprising the axial flow and injected flow together.

2. The cannula of claim 1 wherein at least the initial portion of the central lumen has an inside diameter greater than a diameter of the central passage.

3. The cannula of claim 1 wherein the axial flow and the injected flow have respective flow coefficients that are substantially equal.

4. The cannula of claim 1 wherein the axial flow and the injected flow have respective flow coefficients in a ratio of about 3-to-2, so that the cannula is adapted to be used for venous blood drainage with the first region corresponding to an inferior vena cava and the second region corresponding to a superior vena cava.

5. The cannula of claim 1 wherein the second plurality of fenestrations are oriented perpendicularly to the axial flow, and wherein the outer passages each include a respective curved wall for guiding the fluid received from the second region into the injected flow.

6. The cannula of claim 1 wherein the plurality of second fenestrations are substantially equally spaced circumferentially around the outer lumen wall, and the outer passages are each axially aligned with a respective second fenestration.

7. The cannula of claim 1 wherein each of the outer passages has a cross-sectional area perpendicular to its flow direction that is substantially constant from its respective second fenestration to its outlet.

8. The cannula of claim 1 wherein the aggregate flow coefficient of the outer passages is manually variable in order to adjust the ratio of the axial flow to the injected flow.

9. The cannula of claim 7 wherein the area of the second plurality of fenestrations are variable.

10. The cannula of claim 1 wherein the inner annular wall has a downstream end that extends beyond the outlets of the outer passages.

11. The cannula of claim 1 wherein the downstream end of the inner annular wall has a narrowing wall thickness between the outlets of the outer passages and the termination of the downstream end.

12. The cannula of claim 1 wherein the first stage and the second stage are separately formed from biocompatible molded material.

13. A single-lumen, multi-stage cannula comprising:
a first stage comprising a longitudinal tubular tip having a first plurality of fenestrations disposed at a distal end of the tip for supplying fluid from a first region outside the cannula to provide an axial flow at a proximal end of the tip;
a second stage coaxial with the first stage comprising a first nozzle section having an outer lumen wall and an inner annular wall, wherein a first central passage is disposed within the inner annular wall, wherein the first central passage continues the axial flow from the first stage, wherein a plurality of first outer passages are disposed between the outer lumen wall and the inner annular wall so that the inner annular wall isolates the first central passage from the first outer passages, wherein the outer lumen wall includes a plurality of second fenestrations, wherein each second fenestration supplies fluid from a second region outside the cannula to a respective first outer passage, and wherein the first outer passages have respective outlets arranged to provide a first injected flow substantially parallel to the axial flow;

a third stage coaxial with the second stage comprising a second nozzle section having an outer lumen wall and an inner annular wall, wherein a second central passage is disposed within the inner annular wall, wherein the second central passage continues the axial flow and the first injected flow from the second stage, wherein a plurality of second outer passages are disposed between the outer lumen wall and the inner annular wall so that the inner annular wall isolates the second central passage from the second outer passages, wherein the outer lumen wall includes a plurality of third fenestrations, wherein each third fenestration supplies fluid from a third region outside the cannula to a respective second outer passage, and wherein the second outer passages have respective outlets arranged to provide a second injected flow substantially parallel to the combined first injected flow and axial flow; and a proximal tube coaxial with the third stage and having a central lumen delivering a drainage output of the cannula, wherein the initial portion of the central lumen continues the combined first injected flow and axial flow and receives the second injected flow annularly injected around and substantially parallel with the combined first injected and axial flow.

14. The cannula of claim 13 wherein at least the initial portion of the central lumen has an inside diameter greater than a diameter of the second central passage.

15. The cannula of claim 13 wherein the second and third pluralities of fenestrations are oriented perpendicularly to the axial flow, and wherein the first and second outer passages each include a respective curved wall for guiding the fluid received from the respective regions into the respective injected flow.

16. The cannula of claim 13 wherein the respective inner annular walls have respective downstream ends that extends beyond the respective outlets of the outer passages.

* * * * *